(12) United States Patent
Nelson et al.

(10) Patent No.: US 7,612,053 B2
(45) Date of Patent: *Nov. 3, 2009

(54) 7-SUBSTITUTED FUSED RING TETRACYCLINE COMPOUNDS

(75) Inventors: Mark L. Nelson, Norfolk, MA (US); Laura McIntyre, Cambridge, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/305,048

(22) Filed: Dec. 16, 2005

(65) Prior Publication Data

US 2006/0148765 A1 Jul. 6, 2006

Related U.S. Application Data

(63) Continuation of application No. 10/652,712, filed on Aug. 28, 2003, now abandoned, which is a continuation of application No. 09/852,908, filed on May 10, 2001, now Pat. No. 6,642,270.

(60) Provisional application No. 60/204,158, filed on May 15, 2000.

(51) Int. Cl.
A61K 31/65 (2006.01)
C07D 323/02 (2006.01)

(52) U.S. Cl. ...................... 514/152; 549/434

(58) Field of Classification Search .............. 514/494, 514/152; 549/434
See application file for complete search history.

(56) References Cited

U.S. PATENT DOCUMENTS

| | | | |
|---|---|---|---|
| 2,980,584 A | 4/1961 | Hammer | |
| 2,990,331 A | 6/1961 | Neumann et al. | |
| 3,062,717 A | 11/1962 | Hammer | |
| 3,165,531 A | 1/1965 | Blackwood et al. | |
| 3,338,963 A | 8/1967 | Petisi et al. | |
| 3,341,585 A | 9/1967 | Bitha et al. | |
| 3,345,379 A | 10/1967 | Martell et al. | |
| 3,345,410 A | 10/1967 | Winterbottom et al. | |
| 3,360,561 A | 12/1967 | Zambrano | |
| 3,373,196 A | 3/1968 | Bitha et al. | |
| 3,397,230 A | 8/1968 | Winterbottom et al. | |
| 3,403,179 A | 9/1968 | Zambrano | |
| 3,454,697 A | 7/1969 | Joyner et al. | |
| 3,483,251 A | 12/1969 | Zambrano | |
| 3,518,306 A | 6/1970 | Martell, Jr. et al. | |
| 3,557,280 A | 1/1971 | Weber et al. | |
| 3,579,579 A | 5/1971 | Hlavka et al. | |
| 3,674,859 A | 7/1972 | Beutel et al. | |
| 3,957,980 A | 5/1976 | Noseworthy | |
| 4,018,889 A | 4/1977 | Armstrong | |
| 4,024,272 A | 5/1977 | Rogalski et al. | |
| 4,126,680 A | 11/1978 | Armstrong | |
| 5,532,227 A | 7/1996 | Golub et al. | |
| 5,789,395 A | 8/1998 | Amin et al. | |
| 5,834,450 A | 11/1998 | Su | |
| 6,500,812 B2 | 12/2002 | Nelson et al. | |
| 6,617,318 B1 | 9/2003 | Nelson et al. | |
| 6,624,168 B2 | 9/2003 | Nelson et al. | |
| 6,642,270 B2 * | 11/2003 | Nelson et al. | 514/464 |
| 6,683,068 B2 | 1/2004 | Nelson et al. | |
| 6,818,634 B2 | 11/2004 | Nelson et al. | |
| 6,818,635 B2 | 11/2004 | Nelson et al. | |
| 6,833,365 B2 | 12/2004 | Levy et al. | |
| 6,841,546 B2 | 1/2005 | Draper et al. | |
| 6,846,939 B2 | 1/2005 | Nelson et al. | |
| 6,849,615 B2 | 2/2005 | Nelson et al. | |
| 7,001,918 B2 | 2/2006 | Huss et al. | |
| 7,045,507 B2 | 5/2006 | Draper et al. | |
| 7,056,902 B2 | 6/2006 | Nelson et al. | |
| 7,067,681 B2 | 6/2006 | Nelson et al. | |
| 2002/0128237 A1 | 9/2002 | Nelson et al. | |
| 2002/0128238 A1 | 9/2002 | Nelson et al. | |
| 2002/0132798 A1 | 9/2002 | Nelson et al. | |
| 2004/0048835 A1 | 3/2004 | Nelson et al. | |
| 2004/0063674 A1 | 4/2004 | Levy et al. | |
| 2004/0092490 A1 | 5/2004 | Draper et al. | |
| 2004/0138183 A1 | 7/2004 | Nelson et al. | |
| 2004/0152674 A1 | 8/2004 | Levy et al. | |
| 2004/0176334 A1 | 9/2004 | Nelson et al. | |
| 2004/0214800 A1 | 10/2004 | Levy et al. | |
| 2004/0214801 A1 | 10/2004 | Nelson et al. | |

(Continued)

FOREIGN PATENT DOCUMENTS

| | | |
|---|---|---|
| GB | 921252 | 3/1963 |
| GB | 1469384 | 4/1977 |
| WO | WO-01/19784 A1 | 3/2001 |
| WO | WO-01/87824 A2 | 11/2001 |
| WO | WO-02/04407 A2 | 1/2002 |

OTHER PUBLICATIONS

Koza, Darrell J., "Synthesis of 7-Substituted Tetracycline Derivatives," *Organic Letters*, vol. 2(6):815-817 (2000).

(Continued)

*Primary Examiner*—Celia Chang
(74) *Attorney, Agent, or Firm*—Ivor R. Elrifi; Heidi A. Erlacher; Mintz Levin Cohn Ferris Glovsky and Popeo PC

(57) ABSTRACT

7-substituted fused ring tetracycline compounds, methods of treating tetracycline responsive states, and pharmaceutical compositions containing the 7-substituted fused ring tetracycline compounds are described.

17 Claims, No Drawings

U.S. PATENT DOCUMENTS

| | | |
|---|---|---|
| 2004/0242548 A1 | 12/2004 | Draper et al. |
| 2004/0266740 A1 | 12/2004 | Huss et al. |
| 2005/0020545 A1 | 1/2005 | Draper et al. |
| 2005/0026875 A1 | 2/2005 | Nelson et al. |
| 2005/0026876 A1 | 2/2005 | Nelson et al. |
| 2005/0038002 A1 | 2/2005 | Nelson et al. |
| 2005/0070510 A1 | 3/2005 | Draper et al. |
| 2005/0119235 A1 | 6/2005 | Nelson et al. |
| 2005/0137174 A1 | 6/2005 | Ohemeng et al. |
| 2005/0143352 A1 | 6/2005 | Nelson et al. |
| 2005/0143353 A1 | 6/2005 | Nelson et al. |
| 2005/0148551 A1 | 7/2005 | Nelson et al. |
| 2005/0187198 A1 | 8/2005 | Nelson et al. |
| 2005/0215532 A1 | 9/2005 | Levy et al. |
| 2005/0250744 A1 | 11/2005 | Levy et al. |
| 2005/0288262 A1 | 12/2005 | Bandarage et al. |
| 2006/0003971 A1 | 1/2006 | Nelson |
| 2006/0008463 A1 | 1/2006 | Itoh et al. |
| 2006/0008933 A1 | 1/2006 | Muller et al. |
| 2006/0016694 A1 | 1/2006 | Tanaka et al. |

OTHER PUBLICATIONS

Koza, Darrell J. et al, "Palladium Catalyzed C-N Bond Formation in the Synthesis of 7-Amino-Substituted Tetracyclines," *J. Org. Chem.*, vol. 67:5025-5027 (2002).

Berge, S.M. et al, "Pharmaceutical Salts," *J. Pharm. Sci.*, vol. 66(1):1-19 (1977).

Shezad et al, "Use of fluorinated palladium sources for efficient pd-catalysed coupling reactions in supercritical carbon dioxide," *Tetrahedron Lett.*, vol. 40:2221-2224 (1999).

Silverman, "The Organic Chemistry of Drug Design and Drug Action," *Academic Press*, Chp. 8, pp. 352-400 (1992).

Van den Bogert, C. et al, "Doxycycline in combination chemotherapy of a rat leukemia," *Cancer Res.*, vol. 48:6686-6690 (1988).

\* cited by examiner

7-SUBSTITUTED FUSED RING TETRACYCLINE COMPOUNDS

RELATED APPLICATIONS

This application is a continuation of U.S. patent application Ser. No. 10/652,712, filed Aug. 28, 2003; which is a continuation of U.S. patent application Ser. No. 09/852,908, filed May 10, 2001; which claims priority to U.S. Provisional Patent Application Ser. No. 60/204,158, filed on May 15, 2000. The entire contents each of the aforementioned applications are hereby incorporated herein by reference.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 3,957,980; 3,674,859; 2,980,584; 2,990,331; 3,062,717; 3,557,280; 4,018,889; 4,024,272; 4,126,680; 3,454,697; and 3,165,531. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumbcocci and *Salmonella*). The rise of tetracycline-resistant organisms has resulted in a general decline in use of tetracyclines and tetracycline analogue compositions as antibiotics of choice.

SUMMARY OF THE INVENTION

The invention pertains to, at least in part, 7-substituted fused ring tetracycline compounds of the formula:

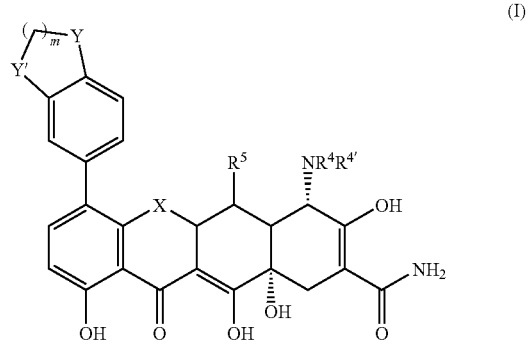

(I)

wherein:
  X is $CR^6R^{6'}$;
  $R^4$ and $R^{4'}$ are each alkyl;
  $R^5$ is hydrogen, hydroxyl, or a prodrug moiety;
  $R^6$ and $R^{6'}$ are each independently hydrogen, hydroxyl, alkyl, or taken together, alkenyl;
  Y and Y' are each independently optionally substituted C, N, O, or S;
  m is 1 or 2; and pharmaceutically acceptable salts thereof.

In a further embodiment, Y and Y' are each oxygen and m is 1.

The invention also pertains to a method for treating a tetracycline responsive state in a mammal, by administering to a mammal a compound of formula I. In another aspect, the invention relates to the use of a compound of formula I to treat a tetracycline responsive state. The invention also pertains to pharmaceutical compositions comprising a compound of formula I, and to the use of a compound of formula I in the manufacture of a medicament to treat a tetracycline responsive state.

DETAILED DESCRIPTION OF THE INVENTION

The invention includes novel 7-substituted fused ring tetracycline compounds and methods of using them. In one embodiment, the invention pertains to 7-substituted fused ring tetracycline compound of the formula:

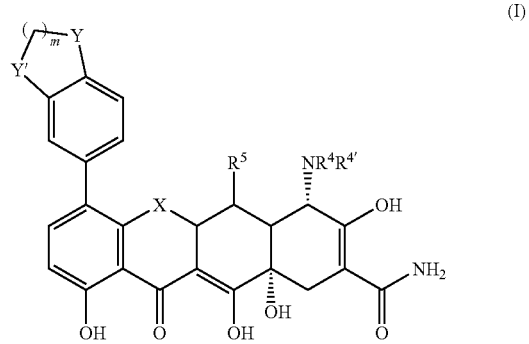

(I)

wherein:

X is $CR^6R^{6'}$;

$R^4$ and $R^{4'}$ are each alkyl;

$R^5$ is hydrogen, hydroxyl, or a prodrug moiety;

$R^6$ and $R^{6'}$ are each independently hydrogen, hydroxyl, alkyl, or taken together, alkenyl;

Y and Y' are each independently optionally substituted C, N, O, or S;

m is 1 or 2; and pharmaceutically acceptable salts thereof.

Examples of $R^6$ and $R^{6'}$ include methyl, ethyl, propyl, butyl, pentyl. Together, $R^6$ and $R^{6'}$ can be methylenyl (e.g., methacycline) which may or may not be further substituted. In a further embodiment, $R^5$, $R^6$ and $R^{6'}$ are each hydrogen. In another embodiment, $R^4$ and $R^{4'}$ are each lower alkyl, e.g., methyl, ethyl, propyl, butyl, pentyl. In yet another embodiment, Y and Y' are each oxygen. In one embodiment, m is 1. In a further embodiment, the compound is 7-3',4'-methylenedioxyphenyl sancycline.

In a further embodiment, Y and Y' are substituted or unsubstituted such that the compound can perform its intended function. For example, if Y or Y' is C or N, the substituent can be hydrogen, alkyl (e.g., methyl, ethyl, propyl, etc.), halogen, hydroxy, or any other substituent which either allows the compound to perform its function or enhances its ability to do so. Furthermore, the 7-substituent may also be substituted at any of the other positions of either ring. Examples of possible substituents include alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, inino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. In an embodiment, m is one and Y and Y' are oxygen. In a further embodiment, the 7-substituent of the tetracycline compound is methylenedioxyphenyl.

The term "tetracycline compound" includes compounds with a similar ring structure to tetracycline, such as those included in formula I. Some examples of tetracycline compounds which can be modified to include a substituent at position 7 include tetracycline, oxytetracycline, methacycline, sancycline, and doxycycline; however, other derivatives and analogues comprising a similar ring structure are also included. Table 1 depicts tetracycline and several known tetracycline derivatives.

TABLE I

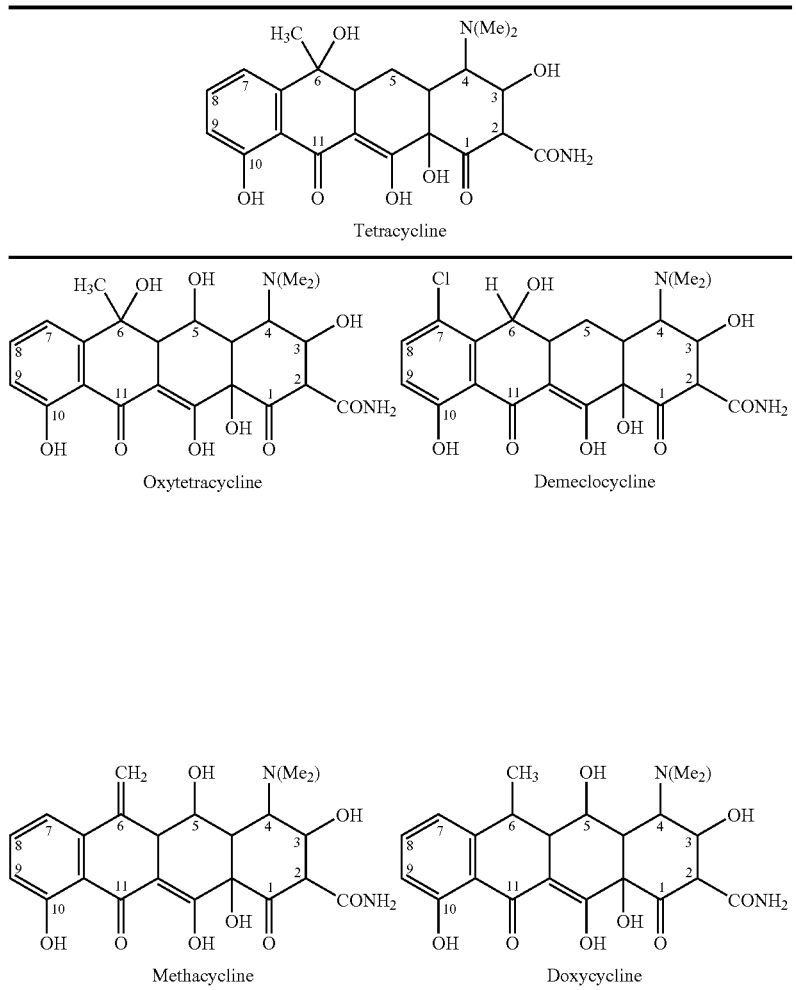

Tetracycline

Oxytetracycline

Demeclocycline

Methacycline

Doxycycline

TABLE I-continued

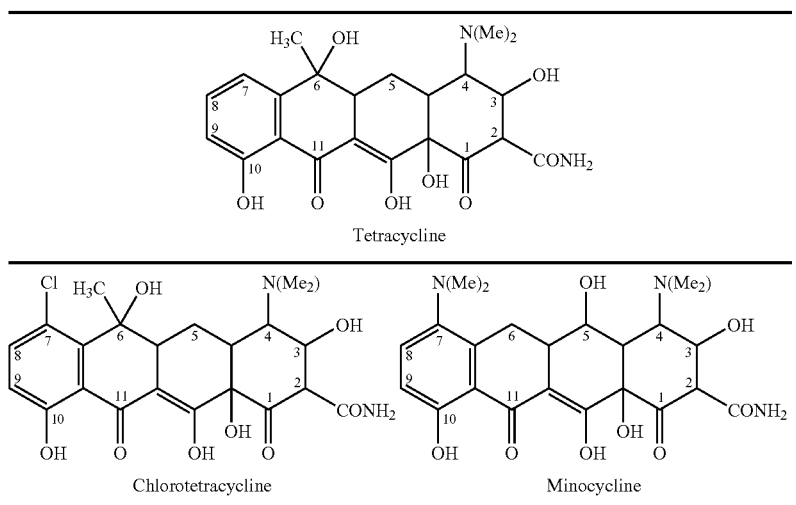

Tetracycline

Chlorotetracycline

Minocycline

The term "7-substituted fused ring tetracycline compounds" includes tetracycline compounds with a fused ring at the 7 position. In an embodiment, the substituted tetracycline compound is substituted tetracycline (e.g., wherein $R^4$ and $R^{4'}$ are methyl, $R^5$ is hydrogen, $R^6$ is methyl and $R^{6'}$ is hydroxyl); substituted doxycycline (e.g., wherein $R^4$ and $R^{4'}$ are methyl, $R^5$ is hydroxyl $R^6$ is methyl and $R^{6'}$ is hydrogen); or substituted sancycline (wherein $R^4$ and $R^{4'}$ are methyl; $R^5$ is hydrogen and $R^6$ and $R^{6'}$ are hydrogen atoms). In another embodiment, the compound is a derivative of tetracycline, minocycline, sancycline, doxycycline, chlortetracycline, oxytetracycline, demeclocycline, or methacycline.

The term "fused ring" includes moieties of the formula:

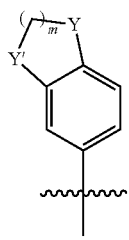

wherein m is 1 or 2, and Y and Y' are each independently selected from the group consisting of substituted or unsubstituted O, N, S, or C. Y and Y' are substituted or unsubstituted such that the compound can perform its intended function. For example, if Y or Y' is C or N, the substituent can be, for example, hydrogen, alkyl (e.g., methyl, ethyl, propyl, etc.), halogen, hydroxy, or another substituent which allows the compound to perform its intended function. Furthermore, the fused ring may also be substituted at any of the other positions of either ring. Examples of possible substituents include alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. In an embodiment, m is one and Y and Y' are oxygen. In a further embodiment, the fused ring is methylenedioxyphenyl.

In one embodiment, the 7-substituted fused ring tetracycline compound is 7-(3',4'-methylene dioxyphenyl)sancycline.

The 7-substituted fused ring compounds of the invention can be synthesized by methods known in the art and/or as described herein. In Scheme 1, a general synthetic scheme is outlined using a Suzuki coupling of a boronic acid with an iodo tetracycline compound. Although the reaction is shown for sancycline, a similar procedure can be used for other tetracycline compounds. Furthermore, other aryl coupling reactions known in the art may also be used.

SCHEME 1

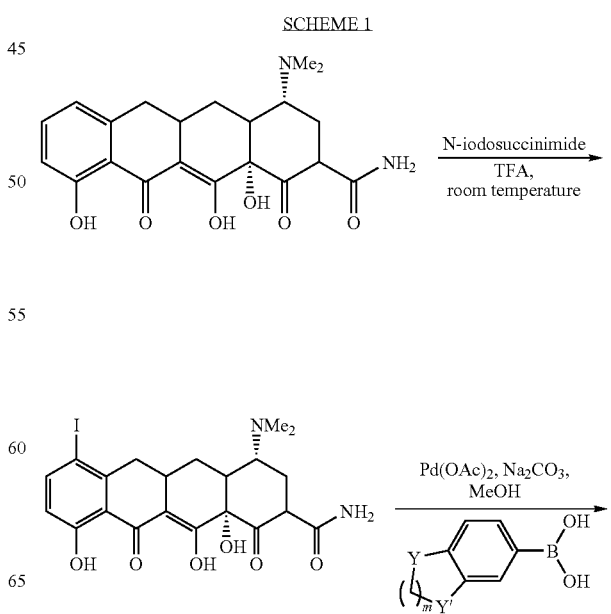

-continued

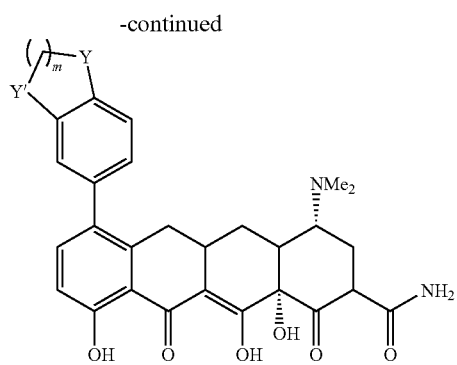

As shown in Scheme 1, an iodosancycline compound can be synthesized from unsubstituted sancycline by treating it with at least one equivalent N-iodosuccinimide (NIS) under acidic conditions. When sancycline was treated with NIS in trifluoroacetic acid, the reaction was carried out initially at 0° C., before being warmed to room temperature for five hours. The reaction is then quenched, and the resulting 7-iodosancycline can then be purified using standard techniques known in the art. The 7-iodosancycline can then be further reacted with a boronic acid, as shown in Scheme 1. 7-iodosancycline, a palladium catalyst (such as Pd(OAc)$_2$), is dissolved in a solvent and treated with aqueous sodium carbonate, and the boronic acid. The resulting compound can then be purified using techniques known in the art such as preparative HPLC and characterized. The synthesis of the compounds of the invention are described in more detail in Example 1.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which comprise oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). The term "alkyl" also includes the side chains of natural and unnatural amino acids.

The term "aryl" includes groups with aromaticity, including 5- and 6-membered single-ring aromatic groups that may include from zero to four heteroatoms as well as multicyclic systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a multicyclic system (e.g., tetralin, methylenedioxyphenyl).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "aLkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkylamino" includes groups and compounds wherein the nitrogen is bound to at least one additional alkyl group. The term "dialkylamino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide" or "aminocarboxy" includes compounds or moieties which contain a nitrogen atom which is bound to the carbon of a carbonyl or a thiocarbonyl group. The term includes "alkaminocarboxy" groups which include alkyl, alkenyl, or alkynyl groups bound to an amino group bound to a carboxy group. It includes arylaminocarboxy groups which include aryl or heteroaryl moieties bound to an amino group which is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "thiocarbonyl" or "iocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term. "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings. Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Examples of heteroatoms include nitrogen, oxygen, sulfur and phosphorus.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

Prodrugs are compounds which are converted in vivo to active forms (see, e.g., R. B. Silverman, 1992, "The Organic Chemistry of Drug Design and Drug Action", Academic Press, Chp. 8). Prodrugs can be used to alter the biodistribution (e.g., to allow compounds which would not typically enter the reactive site of the protease) or the pharmacokinetics for a particular compound. For example, a hydroxyl group, can be esterified, e.g., with a carboxylic acid group to yield an ester. When the ester is administered to a subject, the ester is cleaved, enzymatically or non-enzymatically, reductively or hydrolytically, to reveal the hydroxyl group.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryllower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

The invention also features a method for treating a tetracycline compound responsive state in a subject, by administering to the subject a 7-substituted fused ring tetracycline compound of the invention. Preferably, an effective amount of the tetracycline compound is administered. In an embodiment, the compound is 7-(3',4'-methylene dioxyphenyl)sancycline.

The language "tetracycline compound responsive state" includes states which can be treated, prevented, or otherwise ameliorated by the administration of a tetracycline compound of the invention. Tetracycline compound responsive states include bacterial infections (including those which are resistant to other tetracycline compounds), cancer, diabetes, and other states for which tetracycline compounds have been found to be active (see, for example, U.S. Pat. Nos. 5,789,395; 5,834,450; and 5,532,227). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.*, 48:6686-6690 (1988)).

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., *National Commission for Clinical Laboratory Standards, Document M7-A2*, vol. 10, no. 8, pp. 13-20, 2$^{nd}$ edition, Villanova, Pa. (1990).

The tetracycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or *E. faecalis*. In one embodiment, the tetracycline compound is used to treat a bacterial infection that is resistant to other tetracycline antibiotic compounds. The tetracycline compound of the invention may be administered with a pharmaceutically acceptable carrier.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

The invention also pertains to methods of treatment against microorganism infections and associated diseases. The methods include administration of an effective amount of one or more tetracycline compounds to a subject. The subject can be either a plant or, advantageously, an animal, e.g., a mammal, e.g., a human.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

In one embodiment, the pharmaceutical composition comprises a 7-substituted fused-ring tetracycline compound of the invention, e.g., of formula I. In an embodiment, the compound is 7-(3',4'-methylene dioxyphenyl)sancycline.

The language "pharmaceutically acceptable carrier" includes substances capable of being coadministered with the tetracycline compound(s), and which allow both to perform their intended function, e.g., treat or prevent a tetracycline compound responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline compounds of the invention not specifically described in the foregoing experimental section can be accomplished using combinations of the reactions described above that will be apparent to those skilled in the art.

The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a tetracycline compound of formula I, for the preparation of a medicament. In one embodiment, the tetracycline compound is 7-3',4'-methylenedioxyphenyl sancycline. The medicament may include a pharmaceutically acceptable carrier and the tetracycline compound is an effective amount, e.g., an effective amount to treat a tetracycline responsive state.

In yet another embodiment, the invention also pertains to the use of a tetracycline compound of formula I to treat a tetracycline responsive state, e.g., in a subject, e.g., a mammal, e.g., a human.

Exemplification of the Invention:

Compounds of the invention may be made as described below, with modifications to the procedure below within the skill of those of ordinary skill in the art.

EXAMPLE 1

Synthesis of 7-(3',4'-methylene dioxyphenyl)sancycline 7-iodosancycline

One gram of sancycline was dissolved in 25 mL of trifluoroacetic acid that was cooled to 0° C. (on ice). 1.2 equivalents of N-iodosuccinimide (NIS) was added to the reaction mixture and reacted for forty minutes. The reaction was removed from the ice bath and was allowed to react at room temperature for an additional five hours. The mixture was then analyzed by HPLC and TLC, was driven to completion by the stepwise addition of NIS. After completion of the reaction, the TFA was removed in vacuo and 3 mL of MeOH was added to dissolve the residue. The methanolic solution was then added slowly to a rapidly stirring solution of diethyl ether to form a greenish brown precipitate. The 7-iodo isomer of sancycline is purified by treating the 7-iodo product with activated charcoal, filtering through Celite, and subsequent removal of the solvent in vacuo to produce the 7-isomer compound as a pure yellow solid in 75% yield.

MS (M+H) (formic acid solvent): 541.3

Rt: Hypersil C18 BDS Column, 11.73

$^1$H NMR: 300 MHz (Methanol $d_4$, TMS): δ 7.87-7.90 (d, 1H); 6.66-6.69 (d, 1H); 4.06 (s, 1H); 2.98 (s, 6H); 2.42 (m, 1H); 2.19 (m, 1H); 1.62 (m, 4H); 0.99 (m, 2H).

7-(3',4'-methylene dioxyphenyl)sancycline 200 mg of 7-iodosancycline (0.3 mM), 8.4 mg of Pd(OAc)$_2$ (10% mole equiv.) and MeOH (5 mL) were added to a flask and the system was purged with dry argon while heating externally. Na$_2$CO$_3$ (117 mg, 3 eq.) dissolved in water (2 mL purged with argon) were added to the reaction flask and purged with argon. The boronic acid (3',4'-methylenedioxyphenyl boronic acid) (123 mg, 2 eq.) was dissolved in MeOH (5 mL) and the system was purged with argon for 5 minutes. This solution was then added via syringe to the flask and allowed to react for 1-2 hours. The reaction was then stopped and the solvent was removed in vacuo to produce the crude product. The mixture was purified by preparative HPLC column chromatography using divinylbenzene as a solid phase and a binary solvent system of trifluoroacetic acid (0.1%) and acetonitrile over a gradient of 0% to 100% ACN over 20 minutes. The compound peak eluted at 13.7 minutes. The fractions were removed and the solvent was removed in vacuo and the product isolated as the HCL salt by bubbling HCl gas (anhydrous) through a methanolic solution for 3 minutes and subsequent removal of the solvent. The compound was dried in vacuo to yield the compound as a bright yellow solid in 43% yield.

MS: M+H (formic acid solvent): 535.2

Rt:, divinyl benzene solid-phase 13.7 minutes $^1$H NMR: 300 MHz (methanol $d_4$, TMS) δ 7.47-7.50 (d, 1H), 6.97 (m, 2H), 6.81 (m, 2H), 6.07 (s, 2H), 4.14 (s, 1H), 2.99 (s, 6H), 2.59 (m, 1H), 2.12 (m, 1H), 1.64 (m, 1H).

EXAMPLE 2

In Vitro Minimum Inhibitory Concentration (IC) Assay

The following assay was used to determine the efficacy of tetracycline compounds against common bacteria. 2 mg of each compound was dissolved in 100 µl of DMSO. The solution was then added to cation-adjusted Mueller Hinton broth (CAMHB), which resulted in a final compound concentration of 200 µg per ml. The tetracycline compound solutions were diluted to 50 µL volumes, with a test compound concentration of 0.098 µg/ml. Optical density (OD) determinations were made from fresh log-phase broth cultures of the test strains. Dilutions were made to achieve a final cell density of 1×10$^6$ CFU/ml. At OD=1, cell densities for different genera are approximately:

| | |
|---|---|
| E. coli | 1 × 10$^9$ CFU/ml |
| S. aureus | 5 × 10$^8$ CFU/ml |
| Enterococcus sp. | 2.5 × 10$^9$ CFU/ml |

50 µl of the cell suspensions were added to each well of the microtiter plates. The final cell density was approximately 5×10$^5$ CFU/ml. These plates were incubated at 35° C. in an ambient air incubator for approximately 18 hr. The plates were read with a microplate reader and were visually inspected when necessary. The MIC is defined as the lowest concentration of the tetracycline compound that inhibits growth.

Table 2 shows the relative MIC values for 7-(3',4'-methylene dioxyphenyl)sancycline. For the table, * indicates good inhibition of growth,  indicates very good inhibition of growth, and * indicates exemplary inhibition of growth.

TABLE 2

| ORGANISM | INHIBITION |
|---|---|
| E. coli D1-299 | * |
| E. coli D1-209 | * |
| E. coli pHCM1 | ** |
| S. aureus 12715 | *** |
| E. faec pMV158 | *** |
| E. faec pAM211 | ** |
| E. coli ML308-225 | * |
| S. aureus RN450 | *** |
| E. faecalis ATCC 9790 | *** |
| ATCC 29212 | *** |
| S. aureus 4250 | ** |
| S. aureus ATCC 29213 | *** |
| S. aureus ATCC 13709 | *** |
| S. pnuemoniae ATCC 49619 | *** |
| S. pnuemoniae ATCC 157E | *** |
| E. hirae ATCC 9790 | *** |
| H. influenzae ATCC 49247 | *** |

TABLE 2-continued

| ORGANISM | INHIBITION |
|---|---|
| *M. catarrhalis* ATCC 23246 | ** |
| *E. faecalis* ATCC 9790 | ** |
| mrsa 5 | *** |

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

The invention claimed is:

1. A method for treating a tetracycline responsive state in a mammal, comprising administering to said mammal a 7-substituted fused ring tetracycline compound of formula (I):

(I)

wherein:
X is $CR^6R^{6'}$;
$R^4$ and $R^{4'}$ are each alkyl;
$R^5$ is hydrogen or hydroxyl;
$R^6$ and $R^{6'}$ are each independently hydrogen, hydroxyl, alkyl, or taken together, alkenyl;
Y and Y' are each independently optionally substituted C, N, O, or S;
m is 1 or 2; and pharmaceutically acceptable salts thereof; such that the tetracycline responsive state is a bacterial infection that is selected from the group consisting of *S. pnuemoniae, E. hirae, H influenzae*, and *M catarrhalis*.

2. The method of claim 1 wherein $R^5$, $R^6$ and $R^{6'}$ are each hydrogen and $R^4$ and $R^{4'}$ are each methyl.

3. The method of claim 1, wherein Y and Y' are each oxygen.

4. The method of claim 1, wherein m is 1.

5. A method for treating a tetracycline responsive state in a mammal, comprising administering to said mammal 7-(3',4'-methylene dioxyphenyl)sancycline or a pharmaceutically acceptable salt thereof, such that the tetracycline responsive state is a bacterial infection that is selected from the group consisting of *S. pnuemoniae, E. hirae, H influenzae*, and *M catarrhalis*.

6. The method of claim 2, wherein said bacterial infection is associated with *S. pnuemoniae*.

7. The method of claim 2, wherein said bacterial infection is associated with *E. hirae*.

8. The method of claim 2, wherein said bacterial infection is associated with *H influenzae*.

9. The method of claim 2, wherein said bacterial infection is associated with *M catarrhalis*.

10. The method of claim 2, wherein said bacterial infection is resistant to other tetracycline antibiotics.

11. The method of claim 2, wherein said compound is administered with a pharmaceutically acceptable carrier.

12. The method of claim 5, wherein said bacterial infection is associated with *S. pnuemoniae*.

13. The method of claim 5, wherein said bacterial infection is associated with *E. hirae*.

14. The method of claim 5, wherein said bacterial infection is associated with *H influenzae*.

15. The method of claim 5, wherein said bacterial infection is associated with *M catarrhalis*.

16. The method of claim 5, wherein said bacterial infection is resistant to other tetracycline antibiotics.

17. The method of claim 5, wherein said compound is administered with a pharmaceutically acceptable carrier.

* * * * *